US008428732B2

(12) United States Patent
Nishida et al.

(10) Patent No.: US 8,428,732 B2
(45) Date of Patent: Apr. 23, 2013

(54) NEURAL INTERFACE SYSTEMS AND METHODS

(75) Inventors: Toshikazu Nishida, Gainesville, FL (US); John Gregory Harris, Gainesville, FL (US); Rizwan Bashirullah, Newberry, FL (US); Jose Principe, Gainesville, FL (US); Justin Sanchez, Newberry, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 918 days.

(21) Appl. No.: 12/470,955

(22) Filed: May 22, 2009

(65) Prior Publication Data

US 2009/0292336 A1    Nov. 26, 2009

Related U.S. Application Data

(60) Provisional application No. 61/055,344, filed on May 22, 2008.

(51) Int. Cl.
*A61N 1/00* (2006.01)
(52) U.S. Cl.
USPC .......................................................... 607/45
(58) Field of Classification Search .............. 607/2, 3, 607/45, 72, 62, 61, 54, 48, 46, 116; 600/8, 600/544, 459, 378, 301
See application file for complete search history.

(56) References Cited

U.S. PATENT DOCUMENTS

| 3,667,046 | A * | 5/1972 | Schoolcraft | 375/308 |
|---|---|---|---|---|
| 7,030,411 | B2 * | 4/2006 | Krulevitch et al. | 257/57 |
| 7,324,035 | B2 * | 1/2008 | Harris et al. | 341/155 |
| 2007/0169333 | A1 * | 7/2007 | Donoghue et al. | 29/592 |
| 2009/0124965 | A1 * | 5/2009 | Greenberg et al. | 604/67 |
| 2009/0131995 | A1 * | 5/2009 | Sloan et al. | 607/3 |
| 2009/0319013 | A1 * | 12/2009 | Boling et al. | 607/117 |

FOREIGN PATENT DOCUMENTS

WO    2008042900    10/2008

OTHER PUBLICATIONS

Bashirullah, et al. Florida Wireless Implantable Recording Electrodes (FWIRE) for Brain Machine Interfaces; Department of Electrical and Computer Engineering; Department of Pediatrics Division of Neurology; University of Florida, Gainesville, FL.

Sanchez, et al., "Technology and Signal Processing for Brain-Machine Interfaces", IEEE Signal Processing Magazine, vol. 25, pp. 29-40, Jan. 2008.

* cited by examiner

*Primary Examiner* — George Manuel
*Assistant Examiner* — Robert N Wieland
(74) *Attorney, Agent, or Firm* — Thomas | Horstemeyer, LLP

(57) ABSTRACT

In one embodiment, a neural interface system includes an implantable neural probe having a flexible substrate, electrodes that extend from the substrate that are adapted to contact neural tissue of the brain, a signal processing circuit configured to process neural signals collected with the electrodes, and a wireless transmission circuit configured to wirelessly transmit the processed neural signals, and a backend computing device configured to wirelessly receive the processed neural signals, to process the received signals to reconstruct the collected neural signals, and to analyze the collected neural signals.

26 Claims, 9 Drawing Sheets

NEURAL INTERFACE SYSTEMS AND METHODS

CROSS-REFERENCE TO RELATED APPLICATION

This application claims priority to U.S. provisional application entitled "Wireless Implantable Neural Electrode System" having Ser. No. 61/055,344 and filed May 22, 2008, which is entirely incorporated herein by reference.

NOTICE OF GOVERNMENT-SPONSORED RESEARCH

This invention was made with Government support under NIH Grant No.: NS053561-01A2. The Government has rights in the claimed inventions.

BACKGROUND

The importance of understanding brain function and activity has been long recognized by neuroscientists. One way to obtain such an understanding is to monitor brain signals using a neural interface system that uses a neural probe that directly interfaces with the neural tissue.

Full realization of a neural interface system generally requires determining and specifying how to chronically interface with neural tissue, select the most appropriate control signals, acquire data, and, if desired, deliver therapy via implantable or wearable computers. From an engineering perspective, the functional building blocks of a neural probe are electrodes, amplification stages, encoding algorithm and hardware implementation, and transmission of information to a base station or unit. Although the design constraints are easy to state, they are much more difficult to satisfy in practice.

BRIEF DESCRIPTION OF THE FIGURES

The present disclosure may be better understood with reference to the following figures. Matching reference numerals designate corresponding parts throughout the figures, which are not necessarily drawn to scale.

DETAILED DESCRIPTION

Disclosed herein are neural interface systems, and methods for interfacing with neural tissue. As described below, the systems include an implantable neural device that, in some embodiments, is configured as an ultra-low-power wireless implantable neural probe. The systems provide a neural interface that facilitates diagnosis and/or treatment of a host of neurological problems of the central or peripheral nervous system, such as epilepsy, Parkinson's disease, stroke, movement disabilities, and spinal cord injuries.

The disclosed systems and methods differ significantly from previously proposed systems and methods in several respects. For example, the disclosed systems off-load to a backend computing device much of the processing necessary for implementing the required functionality for neural interfacing thus reducing the power requirements for the implanted system, improving power source lifetime, and reducing the wireless charging interval for rechargeable battery embodiments. In some embodiments, an asynchronous sampling method, referred to herein as integrate-and-fire, is used that enables increased bandwidth, unprecedented miniaturization, and reduction in power consumption for the implanted neural probe.

Another manner in which the disclosed systems and methods differ from previous systems and methods is that a flexible substrate is utilized to integrate electrodes, amplification and signal processing electronics, and wireless transmission and power management electronics. In some embodiments, the electrodes are integrated with the flexible substrate while the electronics are optimized separately and then hybrid packaged using flip-chip bonding or related techniques. Because the substrate is highly compliant, it can flex to accommodate movement of its electrodes that interface with the neural tissue. Accordingly, disruption of neural tissue is reduced or eliminated.

Figure 1:
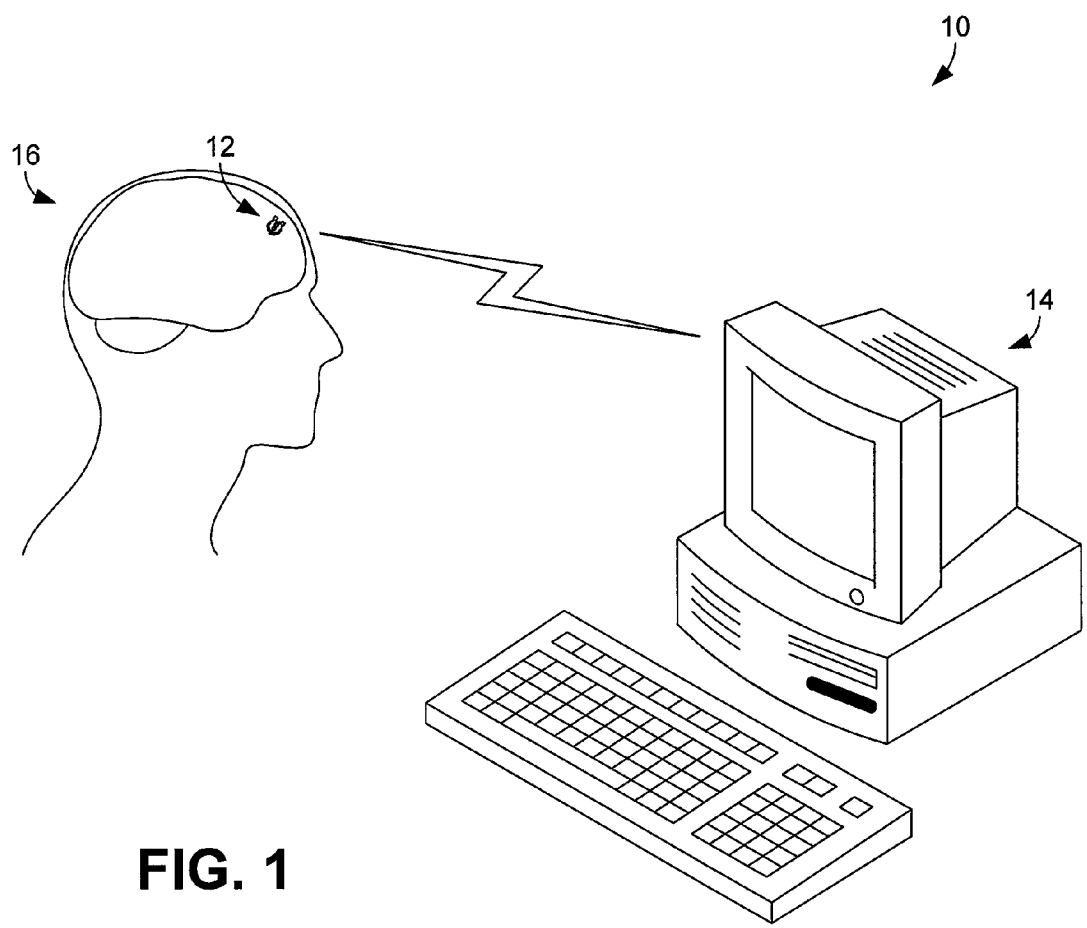
FIG. 1 is schematic view of an embodiment of a neural interface system.

Referring first to FIG. 1, illustrated is an embodiment of a neural interface system 10. As indicated in FIG. 1, the system 10 generally includes an implantable neural device or probe 12 and a computing device 14. As is described in greater detail below, the neural probe 12 is configured to collect analog brain signals (neural signals), translate the signals into a digital pulse train, and then transmit the pulse train to the computing device 14 for further processing. In some embodiments, the neural probe 12 is further configured to deliver therapeutic electronic signals to the neural tissue to stimulate desired neural activity. As shown in the FIG. 1, the neural probe 12 can be implanted in the head of a user or patient 16, for example by mounting the probe on the outer surface of the patient's skull beneath the scalp.

In the example of FIG. 1, the computing device 14 is depicted as a desktop computer. It is noted, however, that a desktop computer is shown as a mere example and comprises just one of many different forms the computing device 14 can take. Generally speaking, the computing device 14 can be substantially any device with computer processing capability that can at least receive (e.g., wirelessly receive) signals transmitted from the implantable neural probe 12 and analyze those signals. In some embodiments, the computing device 14 is further capable of determining an appropriate treatment and transmitting (e.g., wirelessly transmitting) treatment commands back to the probe 12. Examples of other types of computing devices that may be used in the system 10 include portable computing devices, such as notebook computers, wearable computers, implantable computers, handheld computers, personal data assistants (PDAs), mobile phones, robotic prosthetic limbs, and the like. Irrespective of the particular nature of the computing device 14, the computing device provides processing capabilities not possessed by the neural probe 12 due to its size and/or power consumption constraints.

As described below, the neural probe 12 and the computing device 14 are used in concert to provide a neural interface solution. The implantable neural probe 12 can be referred to as the "front end" of the system 10, while the computing device 14 forms the "back end" of the system. Example embodiments for the neural probe 12 and the computing device 14 are described in relation to FIGS. 2-7 in paragraphs that follow.

FIGS. 2-5 illustrate an embodiment of an implantable neural probe 20. With reference first to the exploded view of FIG. 4, the probe 20 generally includes a first or top substrate 22, an internal power source 24, a power source recharging element 26, and a second or bottom substrate 28. The top substrate 22 is thin and composed of a flexible material so that the top substrate is very compliant. As described below, such compliance enables electrodes that directly interface with neural tissue to be embedded within the neural tissue and move along with that tissue to reduce or eliminate irritation and/or damage. In some embodiments, the top substrate 22 is composed of a flexible polymer, such as polyimide, and has a thickness of approximately 10 to 100 microns (μm).

Figure 2:
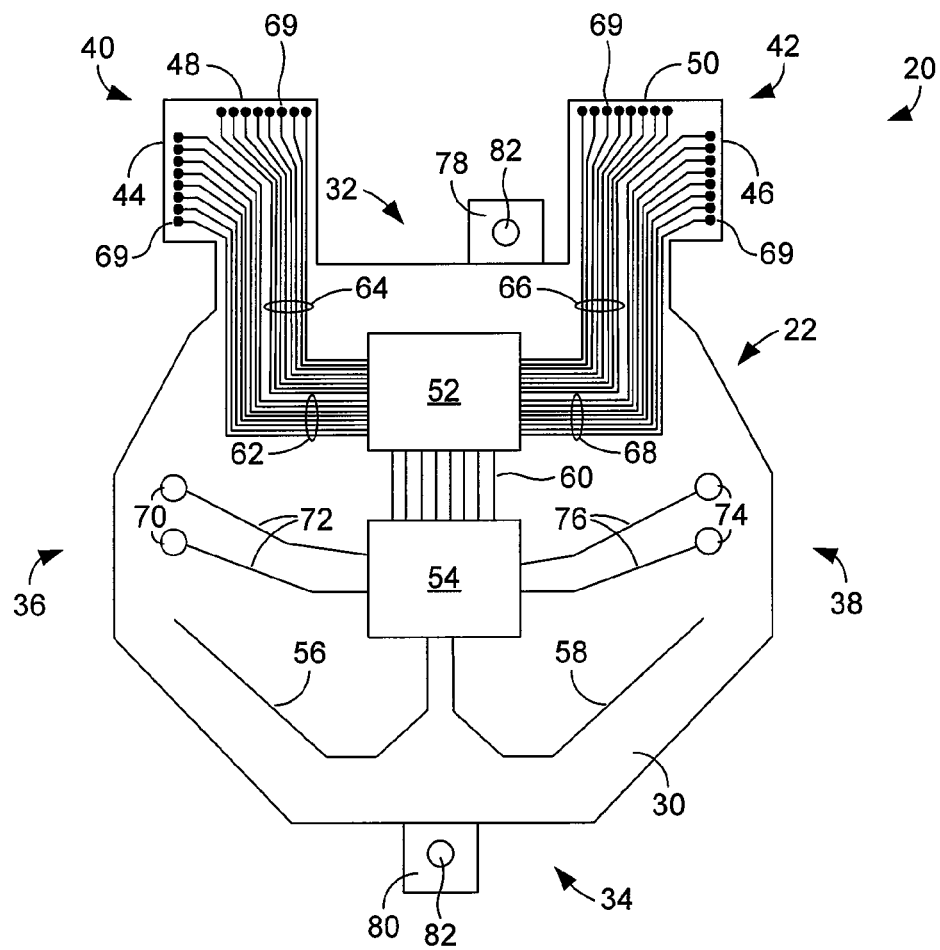
FIG. 2 is a plan view of an implantable neural probe shown in FIG. 1.
Figure 3:
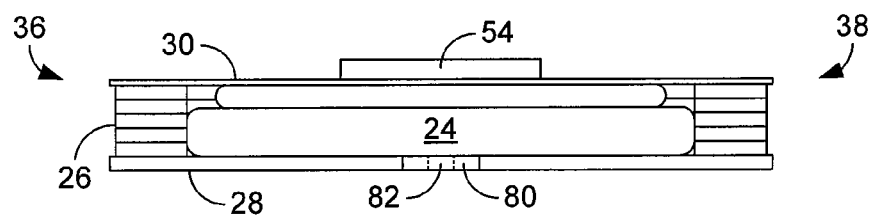
FIG. 3 is an end view of the probe of FIG. 2.

Referring next to FIG. 2, the top substrate 22 comprises a body 30. In the illustrated embodiment, the body 30 is octagonal, although alternative shapes are possible. The body 30 generally defines a first or front end 32 and a second or rear end 34, and opposed lateral sides 36 and 38. Extending from the front end 32 of the body 30 are compliant arms 40 and 42 that provide electrode attachment sites along their lateral edges 44 and 46 and their front edges 48 and 50. In one embodiment, the top substrate 22 is approximately 14.5 millimeters (mm) wide (i.e., from lateral side 36 to lateral side 38) and approximately 18 mm long (i.e., from rear end 34 to the front edges 48, 50 of the compliant arms 40, 42).

Mounted to the top surface of the top substrate 22 are first and second integrated circuit (IC) chips 52 and 54. In some embodiments, each chip 52, 54 comprises a complementary metal-oxide-semiconductor (CMOS) flip chip that has been inverted and attached to the substrate surface using an appropriate bonding mechanism, such as solder pads or bumps. The first chip 52 is a signal processing chip (signal processing circuit) that is configured to receive analog neural signals and translate them into digital pulse trains. The second chip 54 is a wireless transmission chip (wireless transmission circuit) that is configured to transmit the pulse trains to the backend computing device 14 and, in some embodiments, receive treatment commands from that computing device. In some embodiments, the second chip 54 is configured to transmit and receive radio frequency (RF) signals. Each of the chips 52, 54, as well as other components of the neural probe 20, can be encased or encapsulated in an appropriate sealant, such as medical-grade silicone, to form a hermetically-sealed barrier between the components and the patient's body fluids. In some embodiments, the entire probe 20 is encapsulated with the exception of the electrodes that contact the neural tissue (see discussion below).

With further reference to FIG. 2, the top substrate 22 also comprises a plurality of integral conductive traces. The traces can be formed using any one of a number of fabrication techniques, including electroplating using deposited seed material as a template, chemically etching a physically deposited metal, and mechanically imprinting or stamping a conductive film layer. Electroplatable metals include nickel and gold. Physically depositable materials include tungsten, platinum, as well as nickel and gold, while the nano-imprinting or a stamping approach may be applied to a wide variety of conducting materials.

Conductive traces 56 and 58 extend from the wireless transmission chip 54 and serve as antennas for the transmission and receipt of wireless signals. In addition, there are a plurality of traces 60 that extend between the wireless transmission chip 54 and the signal processing chip 52 that enable communication between the two chips. Moreover, there are multiple groups of traces 62, 64, 66, and 68 that extend out from the signal processing chip 52 to the compliant arms 40, 42. In some embodiments, each group comprises eight individual traces, each of which terminates adjacent a side or front edge of the arms 40, 42 with a contact 69 adapted to couple with an associated contact of a modular electrode array. In some embodiments, a group of eight contacts is formed along each of the side edges 44, 46 and each of the front edges 48, 50 to provide four discrete electrode attachment sites.

Figure 4:
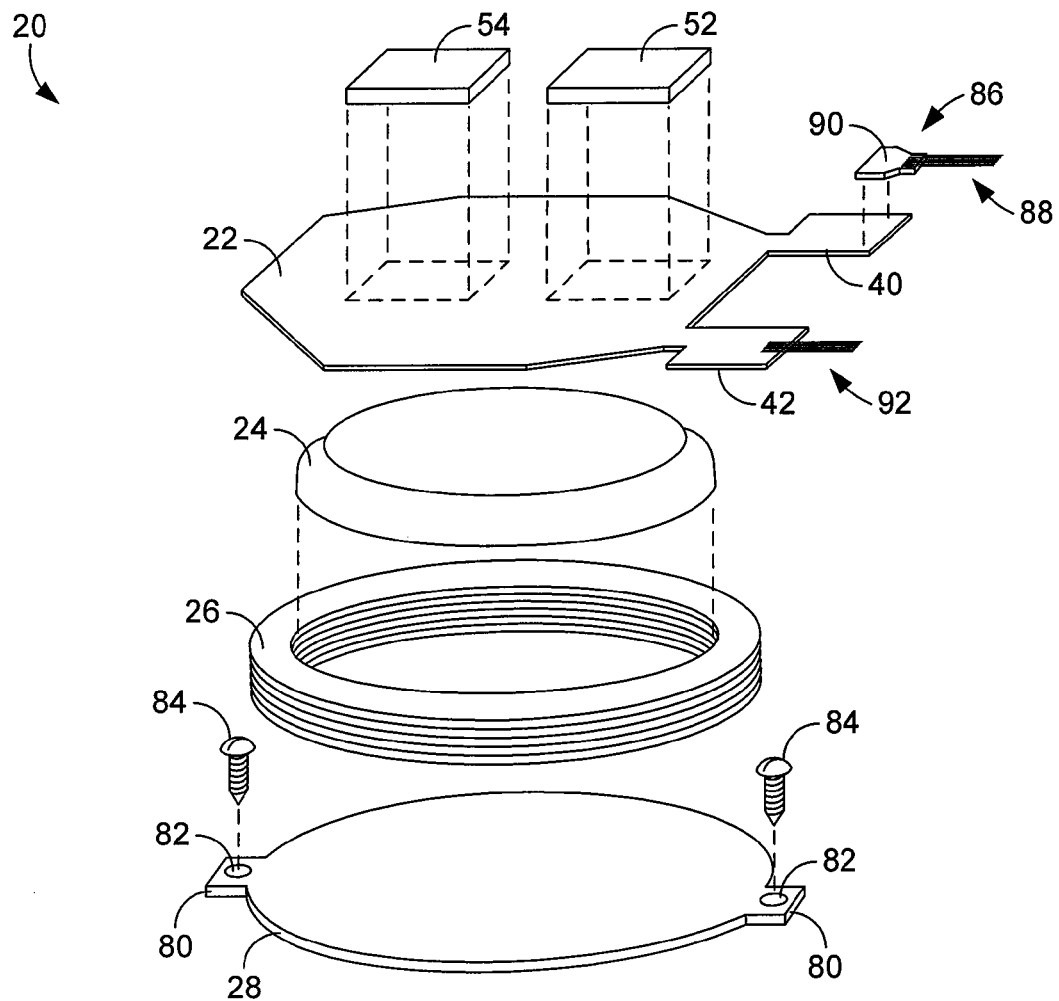
FIG. 4 is a perspective exploded view of the probe of FIG. 2.

The top substrate 22 further includes vias 70 that extend from the top surface of the substrate to the recharging element 26 (FIG. 4). Conductive traces 72 extend from those vias 70 to the wireless transmission chip 54. In addition, the top substrate 22 includes vias 74 that extend from the top surface of the substrate to the power source 24 (FIG. 4). Further conductive traces 76 extend from those vias 74 to the wireless transmission chip 54. In some embodiments, the internal power source 24 comprises a rechargeable battery, such as a low-profile coin battery, and the recharging element 26 comprises an inductive coil that wirelessly recharges the battery when an electromagnetic field is applied to the coil.

The bottom substrate 28 provides structural support to the neural probe 20 and a means for mounting the probe to a support surface, such as the outer surface of the patient's skull. As illustrated in FIG. 4, the bottom substrate 28 comprises front and rear mounting tabs 78 and 80 that each comprise a mounting hole 82 that is adapted to receive a fastener 84, such as a bone screw.

With further reference to FIG. 4, one or more modular electrode arrays 86 can be coupled to the compliant arms 40, 42 of the top substrate 22. Each electrode array 86 includes a plurality of electrodes 88 that extend outward from a body 90 of the array and are adapted to be placed in contact with neural tissue. In some embodiments, the electrodes 88 are adapted to contact the outer surface of the brain in an electrocorticography (ECoG) arrangement. In other embodiments the electrodes 88 are adapted to be embedded in the neural tissue (see discussion of FIG. 6). The electrode arrays 86 can comprise the same number of electrodes as there are contacts 69 at a given electrode attachment site to which the array is mounted. Therefore, in embodiments in which eight contacts 69 are provided along an attachment site, the electrode array 86 can comprise eight electrodes 88. As is further indicated in FIG. 4, the top substrate 22 can alternatively comprise integral electrodes 92 that extend out from the compliant arms 40, 42. In such a case, separate electrode arrays 86 may not be needed. In either case, each electrode 88 can, at least in some embodiments, collect neural signals from multiple neural sites. For instance, neural signals can be separately collected from the tip of the electrode as well as one or more sites along the length of the electrode shaft.

Figure 5:
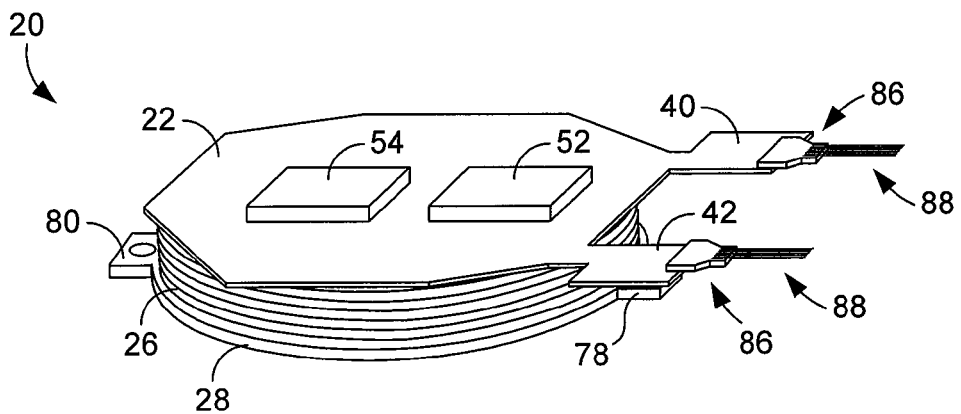
FIG. 5 is a perspective view of the probe of FIG. 2.
Figure 6:
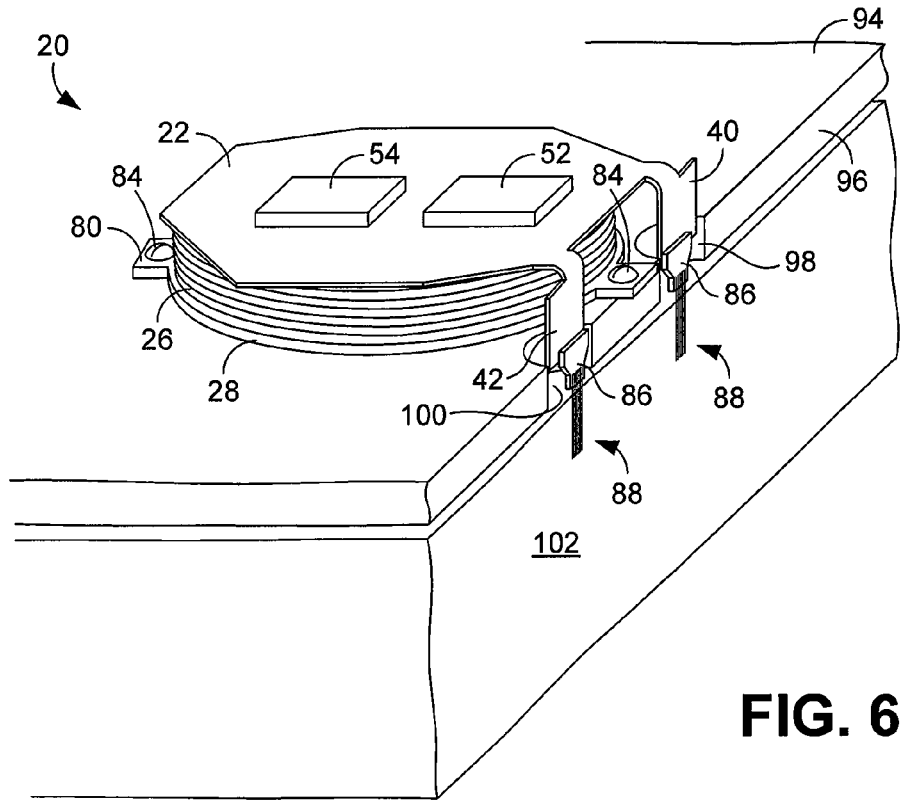
FIG. 6 is a schematic perspective view illustrating an example implementation of the probe of FIG. 2.

FIG. 5 shows the assembled neural probe 20 with two modular electrode arrays 86 attached to the top substrate 22, one coupled to each compliant arm 40, 42. FIG. 6 illustrates an example implementation of the assembled probe 20 of FIG. 5. As indicated in FIG. 6, the neural probe 20 has been mounted to the outer surface 94 of the skull 96 beneath the scalp (the skull being shown in cross-section; the scalp not shown) using the fasteners 84. Holes 98 and 100 have been formed (e.g., drilled) through the skull 96 to accommodate each of the compliant arms 40, 42, which have been bent downward into the holes so that the electrodes 88 of the electrode arrays 86 are embedded within the neural tissue of the brain 102 (also shown in cross-section). As is apparent from FIG. 6, the arms 40, 42 have been bent such that they form an approximately 90 degree angle with the substrate body 30. Because the top substrate 22, and therefore the arms 40, 42, are very compliant, such bending does not damage the substrate 22 and the arms impart little force or torque to the neural tissue so as to minimize disruption. The compliance of the arms 40, 42 further enables the electrodes 88 to move along with the neural tissue when the brain 102 shifts relative to the skull 96, thereby reducing or eliminating damage that could otherwise be inflicted upon the tissue.

Figure 7:
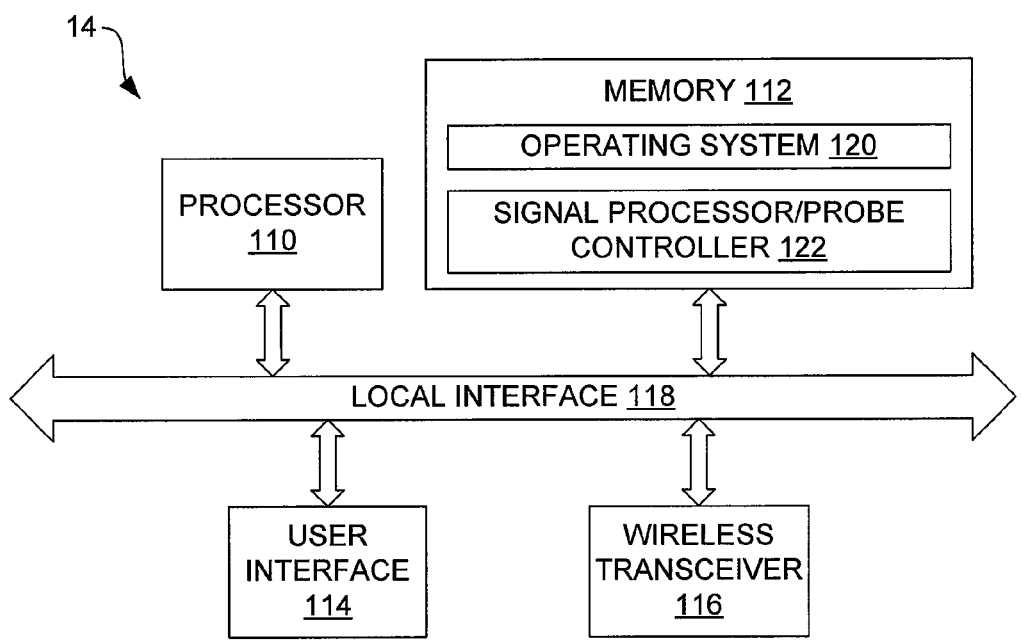
FIG. 7 is a block diagram of an embodiment of a computing device shown in FIG. 1.

FIG. 7 is a block diagram illustrating an example architecture for the computing device 14 shown in FIG. 1. As indicated in FIG. 7, the computing device 14 comprises a processor 110, memory 112, a user interface 114, and a wireless transceiver 116, each of which is connected to a local interface 118.

The processor 110 can include a central processing unit (CPU), a semiconductor-based microprocessor in the form of a microchip, or one or more application-specific integrated circuits (ASICs). The memory 112 includes any one of or a combination of volatile memory elements (e.g., RAM) and nonvolatile memory elements (e.g., hard disk, ROM, etc.).

The user interface 114 comprises the components with which a user (e.g., patient or physician) interacts with the computing device 14. By way of example, user interface 114 comprises one or more of buttons, a keyboard, and a display. The wireless transceiver 116 is adapted to facilitate wireless (e.g., RF) communications with the implantable neural probe 12.

The memory 112 comprises various software and/or firmware including an operating system 120 and a signal processor/probe controller 122. As described below in relation to FIG. 14, the signal processor/probe controller 122 is configured to receive data transmitted from the implantable neural probe 12, analyze that data, and, optionally, generate treatment commands to be transmitted back to the probe or to another device.

A significant operative feature of the neural probe 20 is an alternative signal representation, referred to as integrate-and-fire, in which analog waveforms are translated to samples using the signal processing chip 52. According to this technique, the integral of an analog voltage is transformed into a pulse when it reaches a predetermined threshold. Hence the information about amplitude is contained in the timing of the pulse. There are several advantages of the integrate-and-fire representation. Among those advantages, three are noted with particularly: (i) the implementation of the integrate-and-fire signal representation in analog very-large-scale integration (VLSI) is trivial compared with an analog-to-digital converter (ADC), resulting in substantial power savings; (ii) the data rates decrease drastically because the information is in the timing of pulses and transmission of a continuous sequence is not necessary; and (iii) wireless asynchronous communications are possible, which simplifies the circuitry of the wireless transmission chip 54.

In some embodiments, the signal processing chip 52 comprises a fully-integrated CMOS amplifier with pulse outputs and a time-to-amplitude reconstruction algorithm that recovers the analog signal converted into pulses by the amplifier. Such a design enables recording and processing of signals on the order of tens of microvolts or less. The signals are amplified using a fully integrated preamplifier (hereafter generally referred to as an amplifier) that can reject the DC drift introduced at the electrode and electrolyte interface, but pass low frequency signals down to the millihertz (mHz) range without using any off-chip capacitors. The amplified analog signals are transformed on the chip by a highly compact integrate-and-fire asynchronous voltage-to-time (V/T) converter.

An amplifier-based system having pulsed output includes an amplifier for amplifying a time-varying voltage signal to produce an output voltage signal. A voltage-to-current (V-I) converter converts the output voltage signal into a current signal. An output stage including a current integrator integrates the current signal to generate an integrated voltage. An amplitude-to-time converter generates a pulse train from the integrated voltage, where the timing of the pulses in the pulse train includes embedded information that represents the original time varying voltage signal. The pulse train representation permits transmission and accurate remote reconstruction of the original time-varying voltage signal.

The pulse train generated by the amplitude-to-time converter relies on a simplified design at the front end (neural probe) and a more complex digital reconstruction process at the back end (computing device). Specifically, analog voltages to be processed are embedded into the timing of pulses generated by the system using a very limited number of circuit elements, particularly for the converter function. Therefore, the amplifier and V/T converter together are nearly as small as the amplifier alone thereby providing a desirable alternative to a conventional ADC. Although processing is required to reconstruct the value of the analog signal amplitude, the processing can be performed with a separate device (i.e., backend computing device) that does not have the power or computing limitations of the implantable neural probe.

Figure 8:
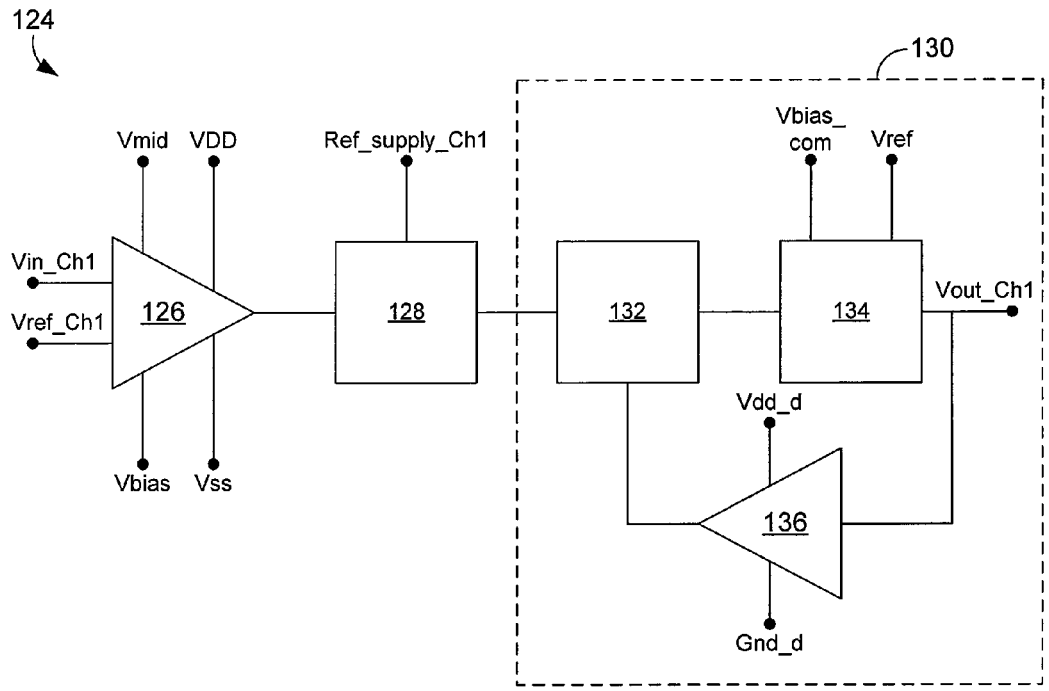
FIG. 8 is a block diagram of a first embodiment of a system for processing neural signals that can be integrated into the probe of FIG. 2.

FIG. 8 shows a high-level block diagram of an amplifier/V/T system 124, which can be comprised by the signal processing chip 52. Due to the very small amplitude of the detected neural signals, it is generally necessary to preamplify the signal (denoted Vin_Ch1) prior to any processing. The first stage in system 124 is an amplifying stage comprising an amplifier 126. In some embodiments, the amplifier 126 provides at least approximately 35 decibels (dB) of gain in the pass band. A V-I converter 128 converts the output voltage signal into a current signal. The amplifier 126 together with V-I converter 128 function as an operation transconductance amplifier (OTA).

An amplitude-to-time converter 130 provides analog-to-digital pulse conversion, preferably using an integrate-and-fire neuron. In the illustrative embodiment, the amplitude-to-time converter 130 includes a current integrator 132 that integrates the current signal provided by the V-I converter 128 to generate an integrated voltage. A comparator 134 together with control logic 136 generates a pulse train at the output of the comparator that can be wirelessly transmitted to the back-end computing device for reconstruction and analysis.

Figure 9:
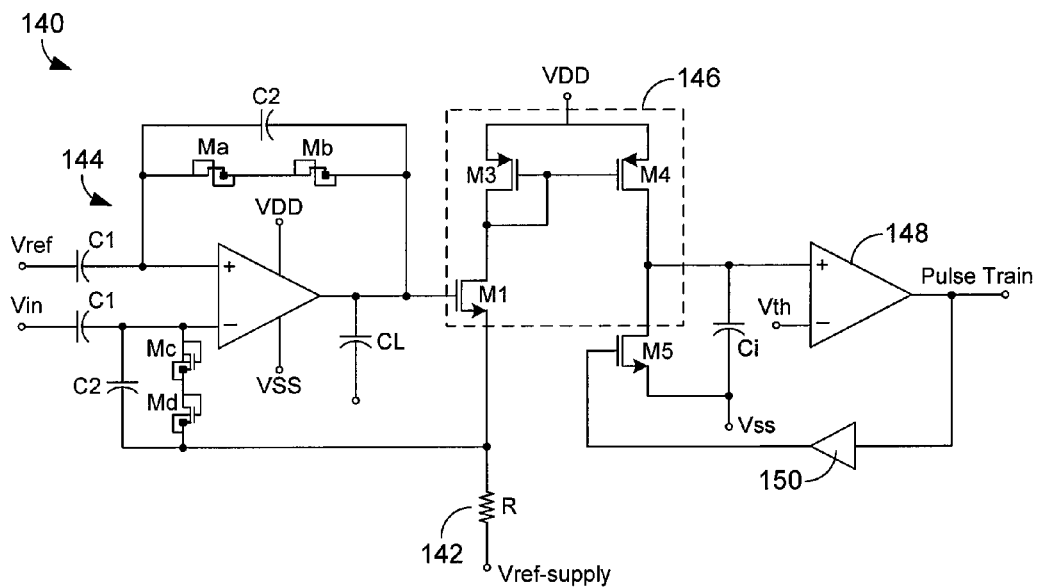
FIG. 9 is a block diagram of a second embodiment of a system for processing neural signals that can be integrated into the probe of FIG. 2.

FIG. 9 is a circuit schematic for an exemplary system 140 that includes an integrated amplifier/amplitude-to-time converter that provides a pulse-coded output. Compared with analog signals, digital signals are much less susceptible to transmission noise. In addition, digital signals are easily storable and provide for more advanced processing algorithms. A popular class of ADC is the Nyquist-Rate converter, which is loosely defined as converters that generate a series of sampled output values that have a one-to-one correspondence to the sampled input voltages. The resolution of the Nyquist-Rate converter is ultimately limited by the power supply. With the improvement of the submicron technologies, high resolution analog circuits are complicated by the reduced low-power supply and poor transistor output resistance, mainly caused by the body-effect. $\Delta-\Sigma$ A/D converters provide a solution to the above problems by relaxing the requirement on the analog circuitry at the expense of more complicated digital circuitry. The system 140 of FIG. 9, however, instead uses simple analog circuitry as well as simple digital circuitry comprising an integrate-and-fire asynchronous mechanism.

Figure 10:
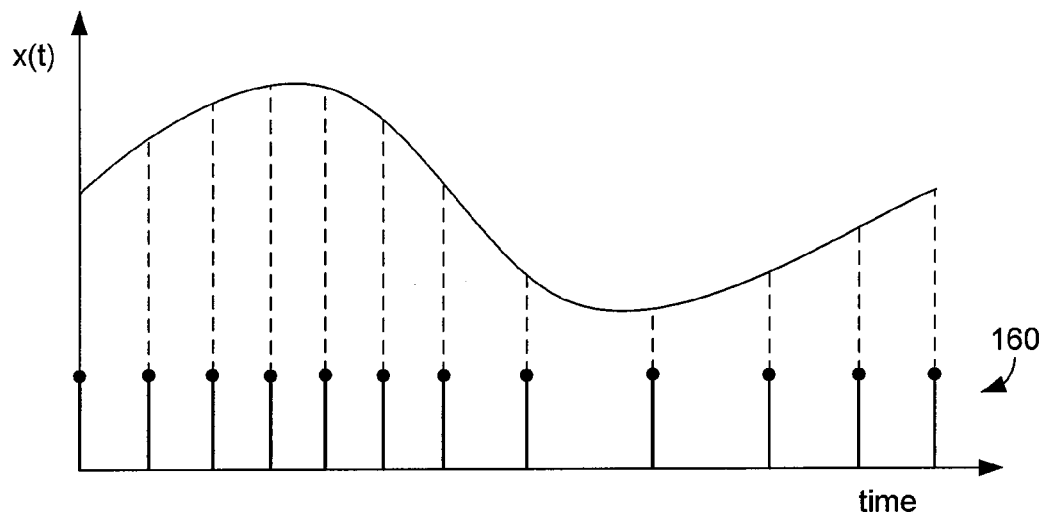
FIG. 10 is a graph that plots an analog input signal along with a corresponding digital pulse train that results when the signal is processed using the system of FIG. 9 or 10.

Turning to FIG. 9, the system 140 comprises a single resistor 142 for converting the output voltage of the amplifier 144 into a current. That current is mirrored by a mirror 146, which comprises transistors M1, M3, and M4. The mirror 146 charges a capacitor Ci until the voltage across Ci reaches Vth, a fixed voltage threshold. Vth is applied to one input of a comparator 148, resulting in the output of the comparator going high. The high voltage at the output of the comparator 148 passes through the buffer 150 and then opens the transistor M5, which quickly pulls the + input of the comparator down to ground. Because the input to the + input of the comparator 148 becomes <Vth, the output of the comparator drops correspondingly, and thus a pulse is completed. This cycle of charging Ci, pulling the output of the comparator 148 high, turning on the transistor M5, and pulling down the output of the comparator to complete individual pulses is repeated to form a pulse train. FIG. 10 illustrates an example pulse train 160 that corresponds to an input analog signal x(t).

The width of the pulses generated by the system 140 is primarily determined by the speed of the comparator 148 and the time delay through the buffer 150. The equations below describe the relationship between the interval of two consecutive pulses (integration time) and the input:

$$v_{out,amp} = A_M v_{in} \quad \text{[Equation 1]}$$

Referring again to FIG. 9, transistor M1 works as a voltage follower and the voltage at the source of M1 is approximately equal to the voltage at the output of the amplifier 144.

$$i_i = (V_{ref\_supply} - V_{mid} + v_{out,amp})/R \quad \text{[Equation 2]}$$

$$\int_k^{k+1} i_i / C_i \, dt = V_{th} \quad \text{[Equation 3]}$$

The following relation results:

$$\int_k^{k+1} (V_{ref\_supply} - V_{mid} + A_M v_{in}) \, dt = V_{th} R C_i \quad \text{[Equation 4]}$$

if the input signal is bounded to a constant b and bandlimited to $\Omega$. Thus, when $$V_{th} < \frac{(V_{ref\_supply} - V_{mid} - b A_M) \Pi}{R C_i \Omega}$$

the original signal can theoretically be reconstructed perfectly.

Further discussion of the integrate-and-fire signal representation and systems that perform translation of analog input signals into digital pulse trains is provided in U.S. patent application Ser. No. 10/844,950, which is hereby incorporated into the present disclosure in its entirety.

The above-described integrate-and-fire signal representation entails passing a regulated analog signal through an integrate-and-fire neuron. The information is losslessly encoded into asynchronous pulse trains fired from the neuron according to specific threshold settings and the pulse train is compatible with digital logic circuits for subsequent processes. Although that coding method has the advantages of low-power consumption and simpler front-end circuitry, the analog signal typically must be made strictly positive by adding a DC bias. Therefore, overall power will be wasted since the signal has to be shifted up by a worst-case offset, which is the most negative signal value possible during operation of the probe. A problem with this approach is that the DC bias tends to continuously produce spikes in the signal even when the original signal is in an idle state during which there is no useful information conveyed by a sensed signal. Additionally, the DC bias results in an average firing rate that is larger than the Nyquist rate. With some modifications to existing architecture, the DC bias can be eliminated by employing two integrate-and-fire neurons that encode positive and negative signals, respectively. Accordingly, the integrate-and-fire neurons do not respond to the signal when its value is zero. However, an additional problem of the integrate-and-fire signal representation is that the peak firing rate is unbounded. Therefore the system could spike at rates that are much larger than the minimum firing rate for perfect reconstruction. The extra pulses lead to wasted power consumption, wasted data bandwidth, and further problems in multiplexing the data off-chip. This peak spiking rate can be reduced with the addition of a neural refractory period wherein after a neuron fires it is disabled for a period of time. This results in the peak firing rate being limited by the inverse of the refractory period.

The above-described drawbacks can be overcome by transforming the original analog signal into an asynchronous biphasic pulse train. An advantage of such a technique is that it can reduce data bandwidth needed for signal transmission. Another advantage is that the technique allows the sampling rate to be reduced whenever the input signal exhibits low amplitude, typically due to noise in the absence of an information-carrying signal, while maintaining a high sampling rate for input signals exhibiting high amplitude, which is characteristic of signals that convey information. Yet another advantage is provided by the introduction of a refractory period, which enables the bounding of the peak data rate to make sampling more manageable. A lower data rate per channel, moreover, allows more channels to be simultaneously recorded.

Figure 11:
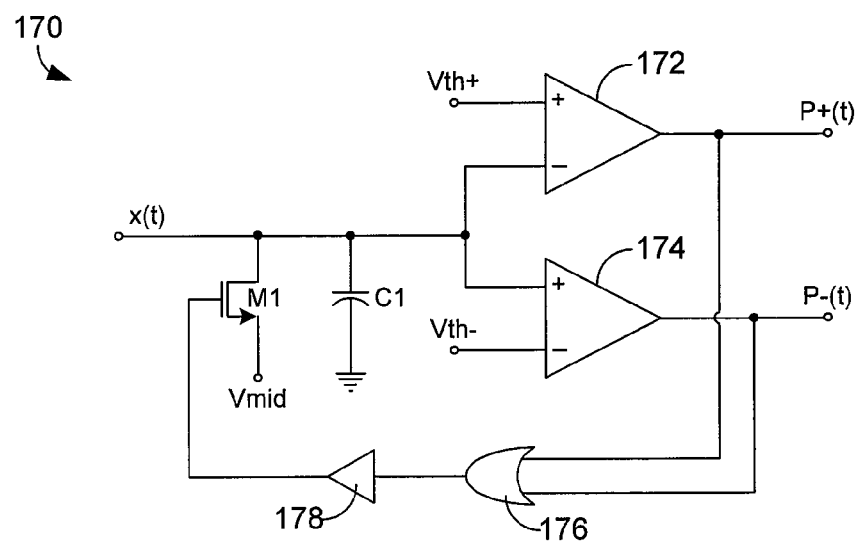
FIG. 11 is a block diagram of a third embodiment of a system for processing neural signals that can be integrated into the probe of FIG. 2.

FIG. 11 provides a schematic diagram of an electronic circuit 170, which may be comprised by the signal processing chip 52, for implementing a biphasic sampling scheme. The circuit 170 illustratively includes two separate comparators: a first comparator 172 and a second comparator 174. The circuit 170 also includes a two-input logic gate 176 having a first input that is connected to the output of the first comparator 172 and a second input that is connected to the output of the second comparator 174. A delay buffer 178 is connected to the output of the logic gate 176. The circuit 170 further includes an integrator comprising a single capacitor C1. The capacitor C1 is connected to a non-inverting input of the first comparator 172 and to an inverting input of the second comparator 174. The capacitor C1 is also connected to the input at which an input signal is received into the circuit 170. Additionally, the circuit 170 includes a switch comprising a transistor M1. The transistor M1 also is connected to the non-inverting input of the first comparator 172 and to the inverting input of the second comparator 174, as well as to the input for receiving an input signal.

Figure 12A:
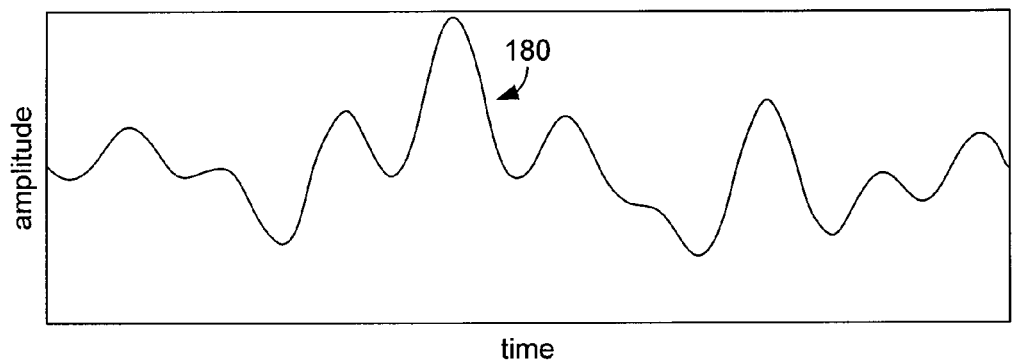
FIG. 12A is a graph that plots an analog input signal.
Figure 12B:
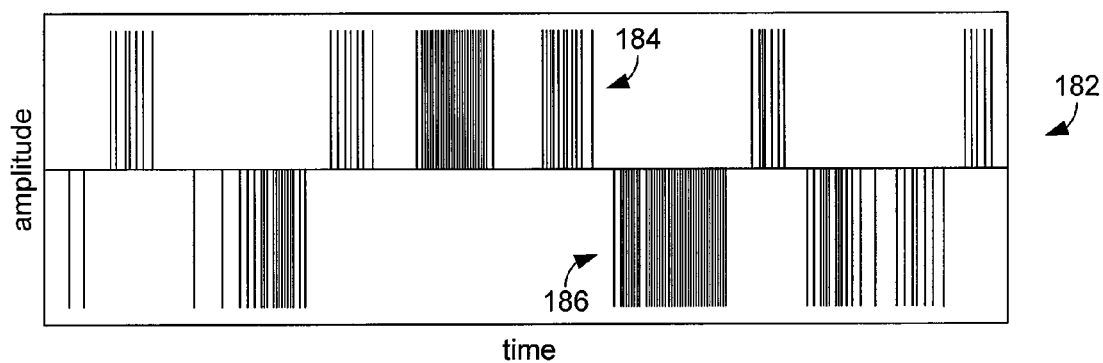
FIG. 12B is a graph that plots a digital pulse train that results when the signal of FIG. 12A is processed using the system of FIG. 11.

Operatively, the integrator C1 generates a response signal by integrating an electrical current input supplied to the input of the circuit 170. If a voltage of the response signal is greater than a predetermined positive voltage threshold, the first comparator 172 generates a positive pulse. If the voltage of the response signal is less than a predetermined negative voltage, then the second comparator 174 generates a negative pulse. FIG. 12B illustrates an example pulse train 182 that corresponds to the analog input signal 180 of FIG. 12A. As shown in FIG. 12B, the pulse train 182 includes both positive pulses 184 and negative pulses 186.

With reference back to FIG. 11, the outputs of both the first and second comparators 172, 174 are fed back to a gate of the transistor M1 through the logic gate 176. The logic gate 176 is an OR gate, which conveys a signal to the gate of the transistor M1 only if there is an output at either the first or second comparators 172, 174. Although the OR gate will convey a signal when there is an output of both comparators 172, 174, the occurrence of simultaneous outputs at the two comparators is precluded since a response signal cannot be both above the positive voltage threshold and below the negative voltage threshold.

When the logic gate 176 supplies a control signal to the gate of the transistor M1, the transistor conducts current, allowing the capacitor C1 to discharge. This is functionally equivalent to resetting of an integrator after a pulse is generated at the output a comparator. The conveyance of the signal from the output of either of the comparators 172, 174 to the gate of the transistor M1 is delayed by the delay buffer 178. The delay can be set to ensure that the width, or refractory period, of each pulse is less than the time interval between successive pulses.

Further discussion of biphasic sampling and systems that enable such sampling is provided in U.S. patent application Ser. No. 12/063,099, which is hereby incorporated into the present disclosure in its entirety.

Figure 13:
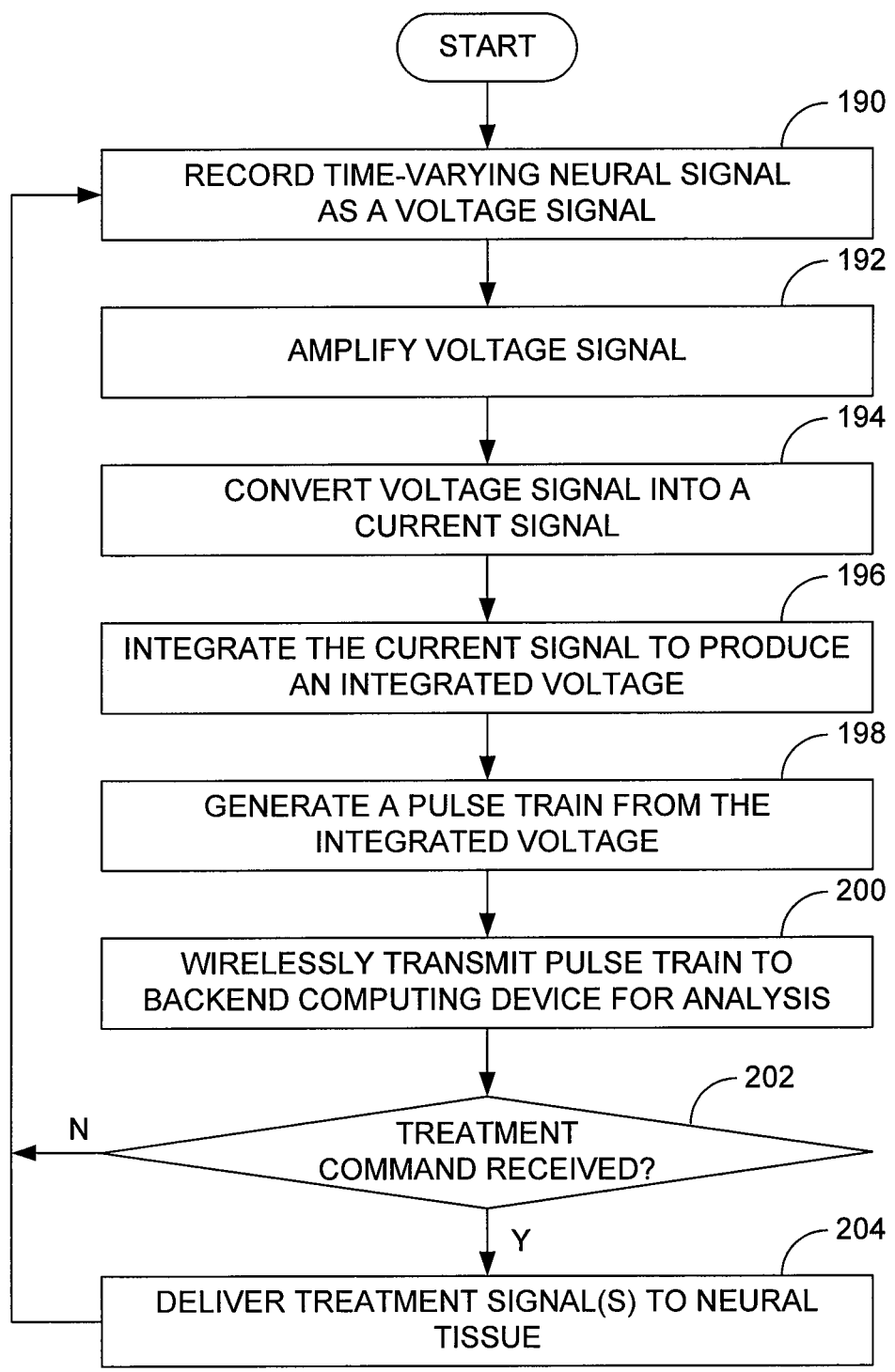
FIG. 13 is flow diagram of an embodiment of operation of an implantable neural probe of a neural interface system.

FIG. 13 provides an example of operation of the implantable neural probe consistent with the foregoing disclosure. Beginning with block 190, the probe records a time-varying neural signal as a voltage signal. By way of example, the probe collects the neural signal using one or more of the electrodes that extend out from the compliant arms of the probe's top substrate. As described above, such electrodes may be embedded within the neural tissue. Using the signal processing chip, the probe then amplifies the voltage signal, as indicated in block 192, and converts the voltage signal into a current signal, as indicated in block 194. The signal processing chip of the probe then integrates the current signal to produce an integrated voltage, as indicated in block 196, and then generates a pulse train from the integrated voltage, as indicated in block 198. Next, in block 200, the wireless transmission chip 54 of the probe wirelessly transmits the pulse train to the backend computing device for analysis.

Figure 14:
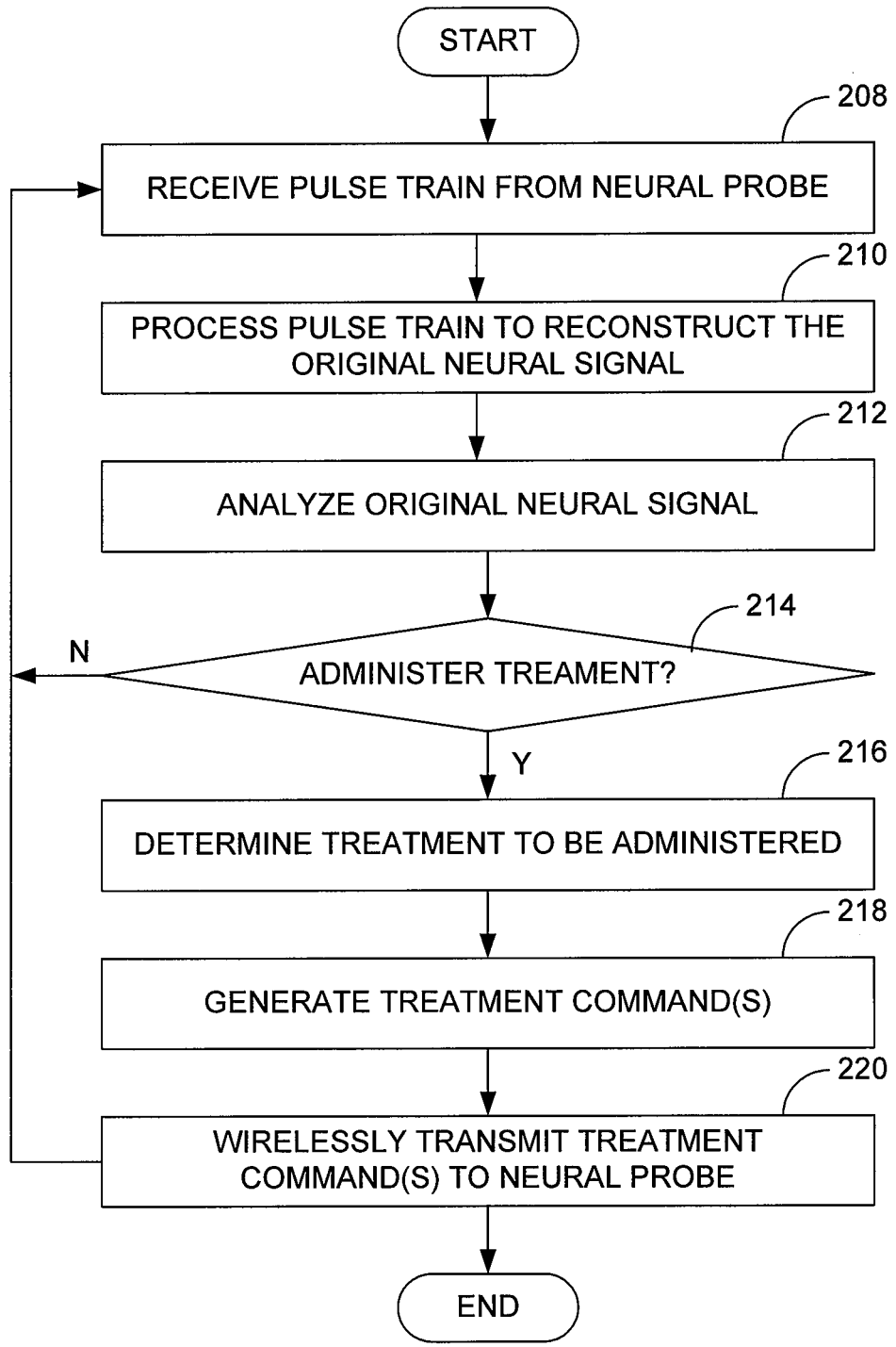
FIG. 14 is a flow diagram of an embodiment of operation of a backend computing device of a neural interface system.

Reference is now made to FIG. 14, which describes an example of operation of the backend computing device. Referring to block 208, the computing device receives the pulse train from the neural probe. The computing device, and more particularly the signal processor/probe controller of the device, then processes the pulse train to reconstruct the original neural signal, as indicated in block 210. Example processes in which such reconstruction is performed are described in U.S. patent application Ser. No. 11/909,060 and Publication No. WO/2008/042900, both of which are hereby incorporated into the present disclosure in their entireties.

Once the original neural signal has been reconstructed, the signal can be analyzed to diagnose any neurological disorders or other problems, as indicated in block 212. Such analysis includes classifying neural spikes, which in some embodiments can be performed using template matching. Irrespective of the analysis that is performed, it can be determined whether to administer treatment, as indicated in decision block 214. In some embodiments, treatment can take the form of electrical signals that are transmitted to the neural tissue by the neural probe to stimulate a desired neural activity. In other embodiments, treatment can comprise delivering electrical signals to other parts of the body, delivering one or more chemical agents (e.g., drugs) to the neural tissue or another part of the body, actuating a mechanical actuator of a prosthetic device (e.g., prosthetic limb), or any other treatment that is appropriate based upon the observed neurological problem.

If no treatment is to be administered, flow returns to block 208 at which the computing device can receive further pulse trains. If, on the other hand, treatment is to be administered, flow continues to block 216 at which the treatment to be administered is determined. Such a determination can, in some embodiments, be made by the signal processor/probe controller automatically based upon the results of the analysis that was performed. Once an appropriate treatment has been determined, treatment commands for the neural probe (or other device) can be generated, as indicated in block 218, and the commands can be wirelessly transmitted to the probe (or other device), as indicated in block 220.

With reference back to FIG. 13 and block 202, flow depends upon whether a treatment command has been received. If not, flow can return to block 190 at which the neural probe records new neural signals. If so, however, flow continues to block 204 at which a treatment signal is delivered to the neural tissue by the probe in accordance with the commands received from the backend computing device.

While particular embodiments have been disclosed in detail in the foregoing description and drawings for purposes of example, those skilled in the art will appreciate that variations and modifications may be made without departing from the scope of the disclosure. All such variations and modifications are intended to be included within this disclosure.

Various software and/or firmware (i.e. logic) have been disclosed. That software/firmware can be stored on any computer-readable medium for use by or in connection with any computer or computer-related system or method. In the context of this disclosure, a computer-readable medium is an electronic, magnetic, optical, or other physical device or means that contains or stores computer instructions.

We claim:
1. A neural interface system comprising:
an implantable neural probe comprising:
    a flexible substrate comprising a body and an integral compliant arm that extends outward from the body, wherein the compliant arm can be bent substantially 90 degrees relative to the substrate body to enable electrode embedding,
    electrodes that extend from the compliant arm in a direction parallel to the arm that are adapted to be embedded in neural tissue of the brain, a signal processing circuit formed or mounted on the flexible substrate, the signal processing circuit being configured to process neural signals collected with the electrodes, and a wireless transmission circuit formed or mounted on the flexible substrate, the wireless transmission circuit being configured to wirelessly transmit the processed neural signals; and a backend computing device configured to wirelessly receive the processed neural signals, to process the received signals to reconstruct the collected neural signals, and to analyze the collected neural signals.

2. The system of claim 1, wherein the compliant arm defines an electrode attachment site and wherein the electrodes are part of a separate modular electrode array that is coupled to the arm.

3. The system of claim 2, wherein the electrode attachment site comprises a plurality of contacts arranged adjacent an edge of the compliant arm.

4. The system of claim 1, wherein the flexible substrate comprises multiple integral compliant arms each being adapted to support electrodes that extend outward from an arm in a direction parallel to the arm and being adapted to be embedded in the neural tissue.

5. The system of claim 1, wherein the signal processing circuit is configured to translate analog neural signals into digital pulse trains that are to be wirelessly transmitted to the backend computing device.

6. The system of claim 5, wherein the signal processing circuit is configured to translate the analog neural signals by:
   amplifying a neural signal to produce an output voltage signal;
   converting the output voltage signal into a current signal;
   integrating the current signal to generate an integrated voltage; and
   generating a pulse train from the integrated voltage, wherein the timing of the pulses in the pulse train identifies an amplitude of the original neural signal.

7. The system of claim 1, wherein the implantable neural probe further comprises an internal power source.

8. The system of claim 7, wherein the internal power source is a rechargeable battery.

9. The system of claim 8, further comprising a recharging element adapted to recharge the rechargeable battery.

10. The system of claim 9, wherein the recharging element is an inductive coil configured to wirelessly recharge the rechargeable battery.

11. The system of claim 1, wherein the implantable neural probe further comprises a second substrate that supports the probe and facilitates mounting of the probe to a patient's skull.

12. The system of claim 1, wherein the backend computing device is further configured to determine an appropriate treatment based upon the neural signal analysis and to wirelessly transmit a treatment command to the implantable neural probe.

13. The system of claim 12, wherein the implantable neural probe is configured to receive the treatment command and deliver electrical signals to the neural tissue to stimulate desired neural activity.

14. An implantable neural probe adapted for implantation beneath the scalp of a patient, the probe comprising:

a flexible substrate having a body and an integral compliant arm that extends out from the body;

electrodes that extend from the compliant arm in a direction parallel to the arm that are adapted to contact neural tissue of the brain;

a signal processing circuit formed or mounted on the flexible substrate, the signal processing circuit being configured to process original neural signals collected with the electrodes;

a wireless transmission circuit formed or mounted on the flexible substrate, the wireless transmission circuit being configured to wirelessly transmit the processed neural signals to a backend computing device; and an internal power source that supplies power to the signal processing and wireless transmission circuits;

wherein the compliant arm can be bent to an approximately 90 degree angle relative to the substrate body to enable embedding of the electrodes into the neural tissue.

15. The neural probe of claim 14, wherein the flexible substrate is composed of polyimide.

16. The neural probe of claim 14, wherein the flexible substrate is approximately 10 to 100 microns thick.

17. The neural probe of claim 14, wherein the flexible substrate comprises multiple integral compliant arms each supporting electrodes that extend out from an edge of the arm in a direction parallel to the arm.

18. The neural probe of claim 14, wherein the signal processing circuit is comprised by an integrated circuit chip mounted to a surface of the flexible substrate.

19. The neural probe of claim 14, wherein the signal processing circuit is configured to translate the original neural signals into digital pulse trains that can be wirelessly transmitted to the backend computing device.

20. The neural probe of claim 19, wherein the signal processing circuit translates the original neural signals by:
   amplifying a neural signal to produce an output voltage signal;
   converting the output voltage signal into a current signal;
   integrating the current signal to generate an integrated voltage; and
   generating a pulse train from the integrated voltage, wherein the timing of the pulses in the pulse train identifies an amplitude of the original neural signal.

21. The neural probe of claim 19, wherein the signal processing circuit generates an asynchronous biphasic pulse train that can be wirelessly transmitted to the backend computing device.

22. The neural probe of claim 14, wherein the internal power source is a rechargeable battery.

23. The neural probe of claim 22, further comprising an inductive coil configured to wirelessly recharge the rechargeable battery.

24. The neural probe of claim 14, further comprising a second substrate that supports the probe and facilitates mounting of the probe to a patient's skull.

25. The neural probe of claim 14, wherein the compliant arm defines an electrode attachment site and wherein the electrodes are part of a separate modular electrode array that is coupled to the arm.

26. The neural probe of claim 25, wherein the electrode attachment site comprises a plurality of contacts arranged adjacent an edge of the compliant arm.

* * * * *

UNITED STATES PATENT AND TRADEMARK OFFICE
CERTIFICATE OF CORRECTION

PATENT NO. : 8,428,732 B2  
APPLICATION NO. : 12/470955  
DATED : April 23, 2013  
INVENTOR(S) : Nishida et al.

It is certified that error appears in the above-identified patent and that said Letters Patent is hereby corrected as shown below:

In the specification

Column 1, lines 15-17:

replace "This invention was made with Government support under NIH Grant No.: NS053561-01A2. The Government has rights in the claimed inventions."

with --This invention was made with government support under grant NS053561-01A2 awarded by the National Institutes of Health. The Government has certain rights in the invention.--

Signed and Sealed this  
Nineteenth Day of January, 2016

Michelle K. Lee  
*Director of the United States Patent and Trademark Office*